United States Patent
Sullivan et al.

(10) Patent No.: US 7,896,836 B2
(45) Date of Patent: *Mar. 1, 2011

(54) VALVED DELIVERY DEVICE AND METHOD

(75) Inventors: Vincent J. Sullivan, Cary, NC (US);
Anjana Bhuta Wills, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1205 days.

This patent is subject to a terminal disclaimer.

(21) Appl. No.: 11/279,471

(22) Filed: Apr. 12, 2006

(65) Prior Publication Data

US 2006/0276755 A1    Dec. 7, 2006

Related U.S. Application Data

(63) Continuation-in-part of application No. 10/685,187, filed on Oct. 14, 2003, now Pat. No. 7,051,734, which is a continuation of application No. 09/950,369, filed on Sep. 10, 2001, now Pat. No. 6,644,309, which is a continuation-in-part of application No. 09/879,517, filed on Jun. 12, 2001, now Pat. No. 6,929,005, which is a continuation-in-part of application No. 09/758,776, filed on Jan. 12, 2001, now Pat. No. 6,722,364.

(51) Int. Cl.
*A61M 37/00* (2006.01)
*A61M 5/315* (2006.01)

(52) U.S. Cl. .......................................... 604/87; 604/236
(58) Field of Classification Search ................... 604/82, 604/83
See application file for complete search history.

(56) References Cited

U.S. PATENT DOCUMENTS

| | | | | |
|---|---|---|---|---|
| 4,526,176 | A | * | 7/1985 | Bremer et al. ............... 600/392 |
| 5,415,162 | A | * | 5/1995 | Casper et al. ............ 128/203.12 |
| 5,531,683 | A | * | 7/1996 | Kriesel et al. .................. 604/89 |
| 6,877,672 | B2 | | 4/2005 | Stihl |

* cited by examiner

*Primary Examiner* — Nicholas D Lucchesi
*Assistant Examiner* — Jenna Zhang
(74) *Attorney, Agent, or Firm* — Robert E. West

(57) ABSTRACT

A valved medicament delivery device including a housing having a chamber including coaxially aligned inlet and outlet, a medicament cartridge located within the chamber having a passage therethrough and membranes sealing the passage having a burst pressure of less than 10 atmospheres, a manually actuatable fluid delivery device having an outlet in fluid communication with the chamber and a manually actuated valve located between the outlet of the fluid delivery device and the chamber inlet for delivery of fluid under pressure to the valve. The medicament delivery device of this invention may be utilized to deliver a controlled unit dose of a medicament on demand by first pressurizing a pressure chamber in the pressure delivery device upstream of the valve, then opening the valve to open the membranes and express the medicament through the chamber outlet.

17 Claims, 4 Drawing Sheets

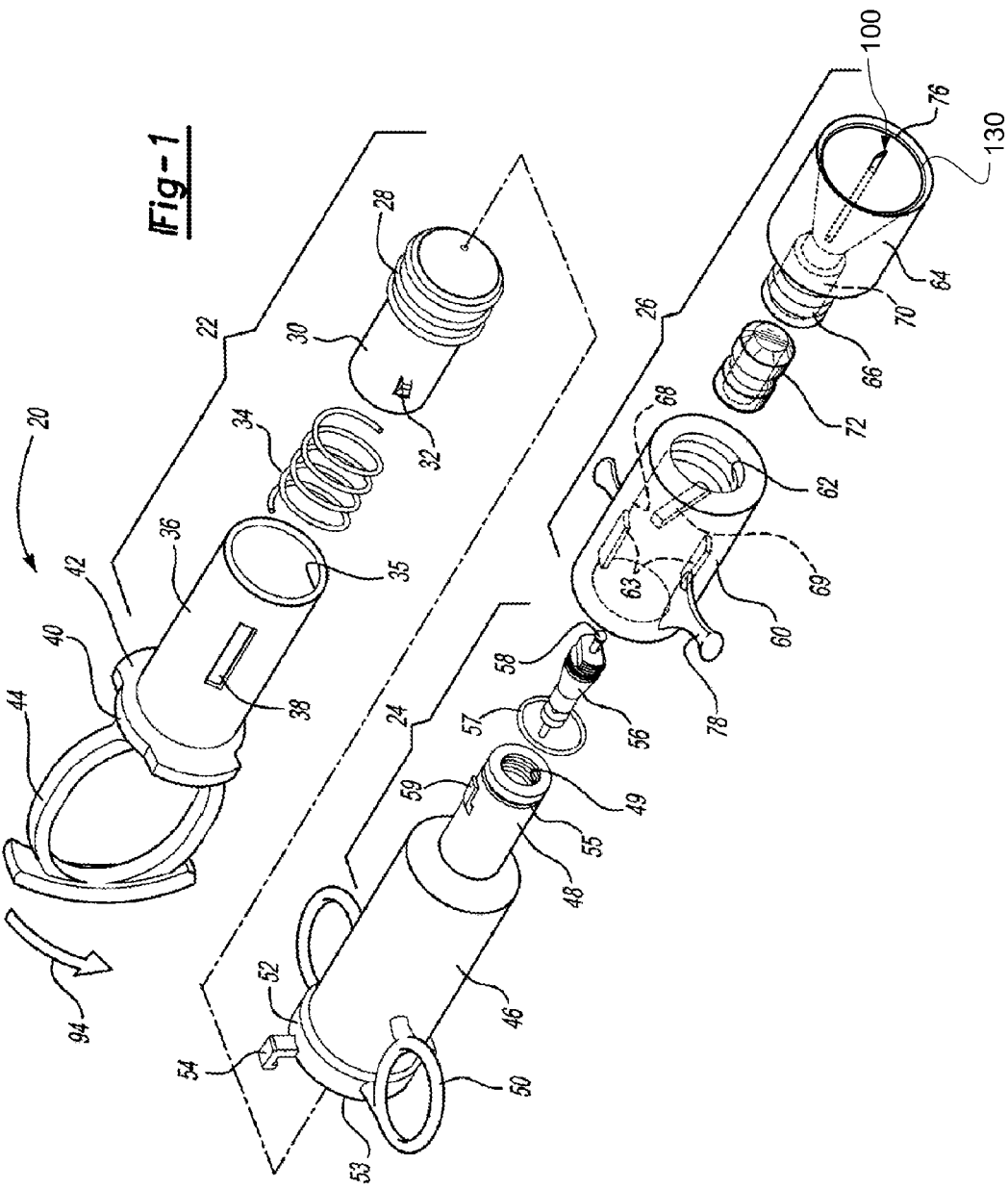

VALVED DELIVERY DEVICE AND METHOD

CROSS REFERENCE TO RELATED APPLICATIONS

Figure 2A:
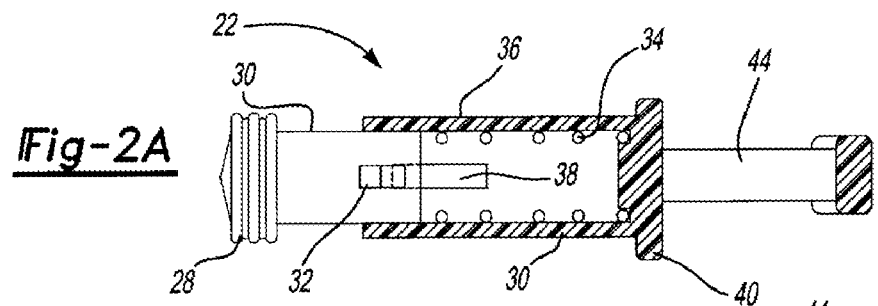

This Application is continuation in part of application of Ser. No. 10/685,187 filed Oct. 14, 2003 now U.S. Pat. No. 7,051,734, which is a continuation application of Ser. No. 09/950,369 filed Sep. 10, 2001 now U.S. Pat. No. 6,644,309, which is a continuation-in-part application of Ser. No. 09/879,517 filed Jun. 12, 2001 now U.S. Pat. No. 6,929,005 which is a continuation-in-part application of Ser. No. 09/758,776 filed Jan. 12, 2001 now U.S. Pat. No. 6,722,364, all four of which are herein incorporated by reference.

FIELD OF THE INVENTION

This invention relates to valved delivery devices, including oral, pulmonary, intranasal, buccal, respiratory, intradermal (ID), subcutaneous (SC) intraperitoneal (IP), intramuscular (IM), Intracardiac (IC), Intravenous (IV), Parenteral or Intraosseous (IO) delivery devices, which releases and delivers on demand a controlled unit dose of medicament to the patient and method of delivery.

BACKGROUND OF THE INVENTION

Syringes are now commonly used primarily to deliver various liquid medicaments via a syringe type device to a patient As used herein, "medicament" includes any powder or liquid medicament, drug or vaccine or combinations thereof which may be administered from a valved device into a patent, sometimes referred to herein as a valved delivery device. More recently, the prior art has proposed unit dose disposable powder medicament delivery devices, such as disclosed in U.S. Pat. No. 5,215,221, wherein a predetermined quantity or unit dose of a powder medicament is sealed in a reservoir formed between opposed thermoplastic sheets and expressed or delivered by application of manual force to a thermoformed blister which, upon activation, breaks a burstable seal between the sheets at the entrance to the reservoir and fluidizes the powder medicament in the reservoir through a delivery tube. The sealed delivery tube is cut prior to use.

There are several considerations affecting the design and efficacy of medicament delivery devices. First, it is important to ensure that a predetermined quantity or dose of medicament is consistently delivered to the user with each application. Second, because injection therapy often requires numerous applications, the cost of providing the dosage should also be considered. Thus, it is desirable that the medicament delivery device consistently expresses substantially the entire medicament to the user and that the delivery device is not susceptible to user error in operation. Third, it is important that the medicament be properly disbursed, dissolved, or entrained in the conveying fluid. Further considerations include the operating complexity, cost of the device, portability and size of the delivery device. It would also be desirable in certain applications to provide a reusable delivery device with a disposable standard medicament cartridge containing a unit dose of medicament which can be easily handled and replaced in the delivery device by the user without error. In other applications, a disposable delivery device is desirable.

Further, it would be desirable for an injection delivery device to deliver a controlled unit dose of a unitized medicament on demand. That is, it would be desirable to be able to charge or pressurize the medicament delivery device prior to use, such that the patient does not have to simultaneously manipulate the pressure delivery means, as by compressing a bulb or syringe, with the device inserted into the body, either via a needle or into a body orifice while delivering the medicament. This can be difficult for some patients to accomplish and may result in poor or partial delivery of the medicament.

The medicament delivery device of this invention provides a reproducible, high level of clearance of medicament or emitted dose from a replaceable cartridge, wherein a manually actuatable fluid pressure delivery device may be charged prior to use and then released on demand to deliver a controlled unit dose of a unitized medicament to the system of the patient.

SUMMARY OF THE INVENTION

As set forth above, the medicament delivery device of this invention may be utilized for oral, pulmonary, intranasal, buccal, intradermal (ID), subcutaneous (SC) intraperitoneal (IP), intramuscular (IM), Intracardiac (IC), Intravenous (IV), Parenteral or Intraosseous (IO) delivery of medicaments, drugs diagnostics, or vaccines and various combinations thereof. The medicament delivery device of this invention includes a medicament housing including a chamber having a chamber inlet and preferably a generally coaxially aligned chamber outlet, a medicament cartridge is preferably located within the housing chamber having opposed ends, a passage through the cartridge through the opposed ends generally coaxially aligned with the chamber inlet and outlet of the housing, a medicament in the cartridge passage and a burstable membrane sealing the passage preferably at both ends of the cartridge having a burst pressure of less than 10 atmospheres. The medicament delivery device further includes a manually actuatable fluid delivery device having an outlet in fluid communication with the chamber inlet for delivery of fluid under pressure to the chamber and a valve located between the outlet of the fluid delivery device and the chamber inlet including a valve inlet in fluid communication with the outlet of the fluid delivery device and an outlet in fluid communication with the chamber inlet of the medicament housing.

Upon actuation of the manually actuatable fluid delivery device, fluid is delivered under pressure to the valve, thereby charging the medicament delivery device for use. Then, upon opening of the valve, fluid is delivered under pressure to the inlet of the chamber containing the cartridge, thereby rupturing the burstable membranes of the cartridge and expressing the medicament through the chamber outlet, and through the conduit (Needle or nozzle). In the preferred embodiment, the manually actuatable fluid delivery device is actuatable to maintain the fluid pressure at the outlet, prior to opening of the valve, to permit the user to insert the needle and release the manually actuatable fluid delivery device in discrete steps.

The medicament delivery device of this invention thereby separates the charging or pressurizing function from the use function. That is, the medicament delivery device of this invention may be utilized by a patient to first "arm" or pressurize the valve inlet and then deliver fluid under pressure to the housing chamber containing the cartridge by opening the valve. Thus, for example, the patient may first arm the medicament delivery device of this invention by manipulating the pressure delivery device to pressurize a chamber at the valve inlet, then turn the device to receive the medicament conduit (needle, mouthpiece or nosepiece) in the user's body and then open the valve to deliver a controlled unit dose of a medicament to the system of the patient through the conduit into the user's body. This simplifies the operation and use of the device to minimize user error and consistently deliver a predetermined quantity or dose of medicament to the patient's system.

As will be understood by those skilled in this art, various fluid delivery devices and valves may be utilized in the medicament delivery device of this invention. For example, the fluid delivery device may include a collapsible bulb which communicates with a pressure chamber through a one way valve having an outlet in communication with the valve inlet. However, in a preferred embodiment of the medicament delivery device of this invention disclosed herein, the manually actuatable fluid delivery device includes a tubular pressure member having an outlet and a plunger or stopper received in the tubular pressure member in sealed relation which is manually reciprocable in the tubular pressure member toward the pressure member outlet. The manually actuatable fluid delivery device may be a conventional syringe preferably having finger grips and a plunger and stopper assembly, such that the patient can hold the barrel and manipulate the plunger with the patient's thumb. Thus, upon movement of the plunger, the stopper is moved in sealed relation toward the syringe outlet, pressurizing the fluid, preferably air, at the syringe outlet. Opening of the valve at the pressure member outlet thus releases or expresses the fluid into the housing chamber containing the cartridge, rupturing the burstable membrane and delivering the medicament to the outlet of the housing as described. In the preferred embodiment, the plunger and stopper assembly and tubular barrel include cooperative stop members which releasably retain the stopper in the barrel when the stopper is moved in the tubular barrel to generate sufficient pressure at the syringe outlet to rupture the burstable membranes. In the disclosed embodiment, the valve is a conventional Schraeder valve operable at pressures of 10 atmospheres or less having a valve stem extending toward the housing, such that movement of the housing toward the manually actuatable fluid delivery device opens the valve and delivers the fluid under pressure to the housing chamber inlet. In the preferred embodiment, the housing includes a bar or finger in the inlet, such that the finger or bar engages the valve stem when the housing is moved toward the manually actuatable fluid delivery device or syringe; however, the valve stem may also engage directly against the burstable membrane at the inlet of the cartridge. Alternatively, the valve stem may extend into the syringe barrel for engagement by the stopper as described further below. As will be understood, however, the valve may be any suitable valve, preferably a manually actuatable valve as discussed further below.

In the disclosed embodiment of the medicament delivery device of this invention, the plunger comprises two telescopic tubular members including a plunger affixed to the stopper and a tubular piston housing which telescopically receives the plunger and the plunger is resiliently biased by a coil spring or the like. The plunger and stopper assembly is assembled by inserting the plunger into the tubular piston housing, compressing the spring and locking the members together by a detent on the plunger which is received in a detent pocket on the tubular piston housing with the spring partially compressed. Then, upon opening of the valve, the sudden drop in pressure allows the spring to drive the stopper to the outlet of the syringe barrel, sweeping the remaining fluid in the barrel through the valve.

As set forth above, in the preferred embodiment of the medicament delivery device of this invention, the manually actuated fluid delivery device is actuatable to maintain the fluid pressure at the outlet prior to opening of the valve to permit the user to release the fluid delivery device and insert the medicament conduit (needle, nozzle, mouthpiece, nosepiece) into the body prior to opening of the valve. In the disclosed embodiment, wherein the manually actuatable fluid delivery device comprises a tubular pressure member, such as a syringe barrel, and a plunger or stopper, interlocking stop members are provided on the syringe barrel and the plunger and stopper assembly which allow the user to fix the plunger when the pressure at the syringe outlet is sufficient to rupture the burstable membranes of the medicament cartridge. This allows the user to fix the stopper in the syringe barrel and maintain the pressure at the syringe barrel outlet while turning the device to receive the outlet of the medicament housing in the nose or mouth prior to opening the valve. In the disclosed embodiment, the valve is a conventional Schraeder valve having a projecting valve stem and the medicament housing is moveable relative to the manually actuatable fluid delivery device to depress the valve stem and open the valve.

The cartridge for the medicament delivery device of this invention is preferably simple in construction, inexpensive and disposable, such that the delivery device is reusable by inserting a new cartridge in the housing chamber following each use. However, the cartridge may be eliminated in a nonreusuable delivery device wherein the burstable membranes are provided at the inlet and outlet to the housing chamber. In the preferred embodiment of the medicament delivery device of this invention, the medicament cartridge includes a body having opposed ends, a passage through the body and through the opposed ends, a medicament stored in the passage and burstable or pierceable membranes covering and sealing the passage at the opposed ends of the body. In the preferred embodiments, the opposed ends of the cartridge body surrounding the passage are convex and the burstable membranes are stretched taut over the convex opposed ends and bonded thereto, sealing the passage. In the disclosed embodiment, the opposed ends of the body are frustoconical surrounding the passage and the membranes comprise a thin polyolefin film heat-sealed or fused to the opposed frustoconical ends of the body. The term polyolefin is understood to mean a polymer containing olefin units such as, for example, ethylene, propylene or 1-butene units or any other alpha-olefin. Polyolefin as used herein includes polyethylene, polypropylene, ethylene-.alpha. olefin copolymer, wherein the alpha olefin having from 3 to 20, preferably 4 to 8 carbon atoms, polyolefin copolymers made by polymerizing olefins in the presence of a metallocene catalyst, ethylene-vinyl acetate copolymer, ethylene-ethyl acrylate copolymer, and ethylene-methyl acrylate copolymer. In particular, it is desirable to use polyethylene, such as low-density, linear-low-density, very-low-density, medium-density, or high-density polyethylene, or polypropylene, such as a polypropylene homopolymer, ethylene-propylene copolymer, or ethylene-propylene block copolymer.

In one preferred embodiment, the polymeric films which form the burstable membranes are preferentially or uniaxially oriented polyolefin films, preferably oriented polyethylene films, angularly related, wherein the films oriented on the opposed ends of the cartridge are most preferably oriented at approximately right angles. It has been found by the applicant that burstable membranes formed of preferentially or uniaxially oriented polyolefin film, most preferably polyethylene film, wherein the films are oriented at approximately right angles, results in improved delivery of the medicament from the body chamber of the delivery device to the system of the user and results in a consistently greater emitted dose. Polyolefin films can be oriented by drawing in one or both mutually perpendicular directions in the plane of the film to impart strength thereto using methods known in the art. Oriented polyolefin films include machine direction and transverse direction orientation. Oriented polyolefin films include uniaxially or biaxially oriented films, with uniaxially films being preferred having a draw ratio of at least 1.2. Uniaxially-oriented films have properties to their advantage for use as the burstable membranes, including relatively high stiffness, as indicated by the tensile modulus in a particular direction, usually the machine direction, compared to the transverse direction. Properties of the oriented polyolefin film can be dependent to a certain degree on the particular process conditions under which the polyolefin film was manufactured. For example, a stiffer film with lower transverse burst pressure properties would result from an orientation process incorporating a larger machine direction orientation draw ratio. Thus, oriented polyolefins films can be tailored to provide an appropriate burst pressure property within a preferred film thickness range.

Based upon computer modeling by the applicant, consistently greater dosing is believed to result from turbulence or "turning" of the delivery fluid through the passage of the cartridge containing the medicament where preferentially oriented polyolefin membranes are used oriented at approximately right angles on the opposed ends of the cartridge. Prototype testing indicates that the burstable membranes at the opposite ends of the cartridge in the delivery devices of this invention rupture nearly simultaneously using only a modest pressure, e.g., less than 5 atmospheres. Where the membranes are preferentially or uniaxially oriented and perpendicular, the membranes each rupture in a slit near the center along the axis of the oriented films at approximately right angles to one another. This requires the fluid (as a gas or liquid), to turn as the fluid is rapidly transmitted through the passage, entraining and/or dissolving the medicament and expressing the entrained medicament through the slit formed in the second membrane. It has been found by the applicant that generally perpendicular orientation of the preferentially or uniaxially oriented films oriented at right angles resulted in an emitted dose of about 97%, in the respiratory embodiment.

In another preferred embodiment, the burstable membranes are formed of a cast polyolefin copolymer of polyethylene and polyethylene methylacrylate copolymer film having a thickness of about 0.5 mil, wherein the films are stretched taut over the passage and heat sealed or fused to the opposed ends of the cartridge. Where the burstable membranes are formed of preferentially or uniaxially oriented polyethylene film, the film preferably has a thickness of about 1 mil. However, it is believed that the burstable membranes may also be formed of other polymers including, for example, polypropylene, acetate, polycarbonate, etc., wherein the film is preferably scored or embossed to reduce the required gas rupture pressure, thus having a rupture pressure of between 1.2 and 10 atmospheres, more preferably less than 5 atmospheres and most preferably between 1.5 and 4 atmospheres. Medicament cartridges employing such low burst pressure films allow for use of simple, manually actuated, pressurization mechanisms as described below. In the preferred embodiment of the cartridge for a medicament delivery device of this invention, the medicament passage or reservoir is generally cylindrical and the cartridge body is also generally cylindrical. An annular groove may be provided at the mid-portion of the body for ease of handling.

As disclosed in the above-referenced co-pending application, U.S. Ser. No. 09/879,517, the medicament cartridge utilized in the medicament delivery device of this invention may be formed by injection molding a generally cylindrical cartridge body having convex end portions and a passage through the end portions. The method then includes applying a thin burstable polyolefin sheet over one end, preferably by stretching a polyethylene sheet over the end and heat bonding the sheet to the convex end of the cartridge body, sealing the first end. The medicament may then be inserted through the open end of the passage and the second end is then sealed as described. Based upon computer modeling by the Applicant, the highest medicament delivery rate in a respiratory embodiment is achieved using one burstable polyolefin membrane at the exit of the delivery device. It would be expected that other embodiments would have similar results. This can be accomplished by the medicament delivery device of this invention by utilizing the valve stem or another piercing member to pierce the burstable membrane at the inlet prior to or during actuation of the pressure member. However, in the disclosed preferred embodiment of the medicament delivery device, the opening of the valve substantially simultaneously bursts both the inlet and outlet membranes avoiding any loss of medicament through the inlet membrane during use.

The preferred embodiments of the medicament delivery device of this invention are particularly, but not exclusively, adapted for respiratory delivery (including pulmonary, intranasal, buccal, and respiratory), oral delivery, parenteral delivery (including intradermal (ID), subcutaneous (SC) intraperitoneal (IP), intramuscular (IM), Intracardiac (IC), Intravenous (IV), Parenteral or Intraosseous (IO)) medicament delivery of a powder medicament. The powder is dispersed by fluid pressure that ruptures the membranes on the opposed ends of the cartridge, creating a substantially instantaneous fluid stream through the cartridge. In the respiratory embodiment, the fluid stream entrains the powder particles into the fluid, which disperses the medicament to the targeted tissue of the patient. In the injection embodiment, the fluid stream entrains and/or dissolves the powder particles into the fluid, which delivers the medicament to the injection site. As will be understood, however, the medicament delivery device of this invention, particularly including the cartridge, can also be utilized for liquid medicament delivery, or a combination thereof.

Other advantages and meritorious features of the medicament delivery device of this invention will be more fully understood from the following description of the preferred embodiments, the claims and the appended drawings, a brief description of which follows.

BRIEF DESCRIPTION OF THE DRAWINGS

FIG. 1 is an exploded perspective view of one embodiment of the medicament delivery device of this invention;

FIG. 2A is a partially cross-sectioned side view of one embodiment of the plunger assembly illustrated in FIG. 1 prior to assembly;

FIG. 2B is a side cross-sectioned view of the plunger assembly shown in FIG. 2A following assembly;

FIG. 3 is a side partially cross-sectioned view of the medicament delivery device shown in FIG. 1 in the "unarmed" state;

FIG. 4 is a side partially cross-sectioned view of the medicament delivery device shown in FIGS. 1 and 3 in the "armed" state;

FIG. 5 is a side partially cross-sectioned view of the medicament delivery device shown in FIGS. 1, 3 and 4 during expressing of the medicament in the medicament cartridge;

FIG. 6 is a side partially cross-sectioned view of the medicament delivery device shown in FIGS. 3 to 5 following delivery of the medicament;

FIG. 7 is a perspective view of the medicament cartridge shown in FIG. 1;

FIG. 8 is a side cross-sectional view of the medicament cartridge shown in FIG. 7 in the direction of view arrows 8-8; and FIG. 9 is a partial side cross-sectional view of the detent locking arrangement for the manually actuatable fluid delivery device illustrated in FIGS. 2A and 2B.

DETAILED DESCRIPTION OF A PREFERRED EMBODIMENT

The embodiment of the medicament delivery device 20 illustrated in FIG. 1 includes a plunger and stopper assembly 22, a barrel and valve assembly 24 and a housing and cartridge assembly 26. The plunger and stopper assembly 22 includes an elastomeric stopper 28 and a plunger or piston 30 having an integral detent 32. A coil spring 34 is received in the open end 35 of the tubular piston housing 36 as described further below and the tubular housing 36 includes a detent pocket 38 and an end wall 40 including radial locking projections or tabs 42 and an integral thumb grip 44.

The barrel and valve assembly 24 includes a tubular barrel 46 including a reduced diameter tip portion 48 having an open end 49, integral finger grips 50 and an integral flange portion 52 having hook-shaped locking tabs 54. The reduced diameter tip portion 48 of the barrel 46 includes an annular groove 55 which receives an O-ring 57 and integral resilient opposed L-shaped tabs 59. The Schraeder valve 56 is received in the open end 49 of the tip portion 48 and retained therein by a press fit and the valve includes a projecting valve stem 58. The housing and cartridge assembly 26 includes a medicament dosing member comprised of a first housing member 60 having a female threaded opening or bore 62 having axially extending rectangular grooves 63 which receive tabs 59 and a second housing member 64 having a male threaded end portion 66 and hub 130 containing needle 100. The first housing member 60 includes a port or passage 68 therethrough which defines the inlet of the medicament dosing member or housing and the second housing member 64 includes a chamber 70 which receives the medicament cartridge 72 coaxially aligned with the passage 68 through the first housing member 60 and a hub receiving portion 76, which is also coaxially aligned with the chamber 70 and the passage 68 when the first and second housing members 60 and 64 are threaded together. Hub 130 is inserted into hub receiving portion 76. Hub 130 holds needle 100, which has a distal end 110 and a proximal end 120. Hub 130 may be a separate component, or may be comprised of an adhesive which fills the hub receiving portion 76 to hold needle 100 in the proper position. Proximal end 120 of needle 100 is in fluid communication with chamber 70. Medicament flows through needle 100 from proximal end 120 to distal end 110. Distal end 110 is normally inserted into the patient. Needle 100 may be of a variety of common gage sizes ranging from 10 to 50 gauges. Needle 100 may be sharpened at the distal tip when used for parenteral delivery. In one aspect of the invention, needle 100 is used for intradermal, subcutaneous or intramuscular injection and is a 28 to 34 gauge needle. In this aspect of the invention, needle 100 extends distally from the medicament device from about 0.3 mm to about 25 mm, so that the outlet of the needle is arranged in the desired target tissue. The length and outlet of the needle is sized in the range above to deliver to the desired target tissue, as described more thoroughly in U.S. patent application Ser. No. 09/893,746 filed Jun. 29, 2001 and U.S. patent application Ser. No. 10/704,035 filed Nov. 6, 2003, both of which are herein incorporated by reference. In another aspect of the invention, needle 100 is used for intra-nasal administration and is a 15-20 gauge needle which is used as a conduit. In a preferred embodiment, the first housing member 60 also includes finger grips 78 which may be integral with the first housing member, as shown. The first housing member 60 further includes an integral bar or finger 69 bridging the internal surface of the inlet opening 68 as best shown in FIGS. 3 to 6. The finger 69 may be integrally molded with the first housing member by injection molding or a separate finger may be inserted through the wall of the tubular first housing member 60.

Figure 2B:
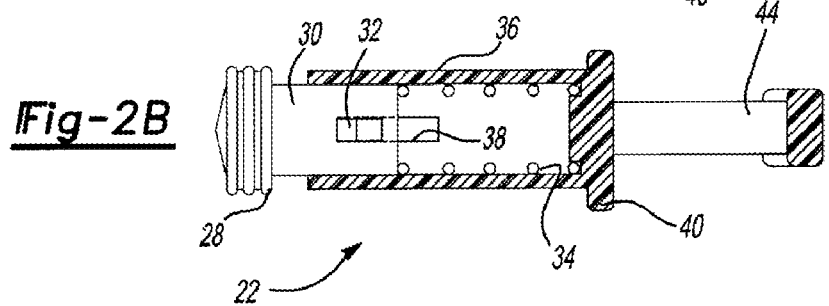
Figure 4:
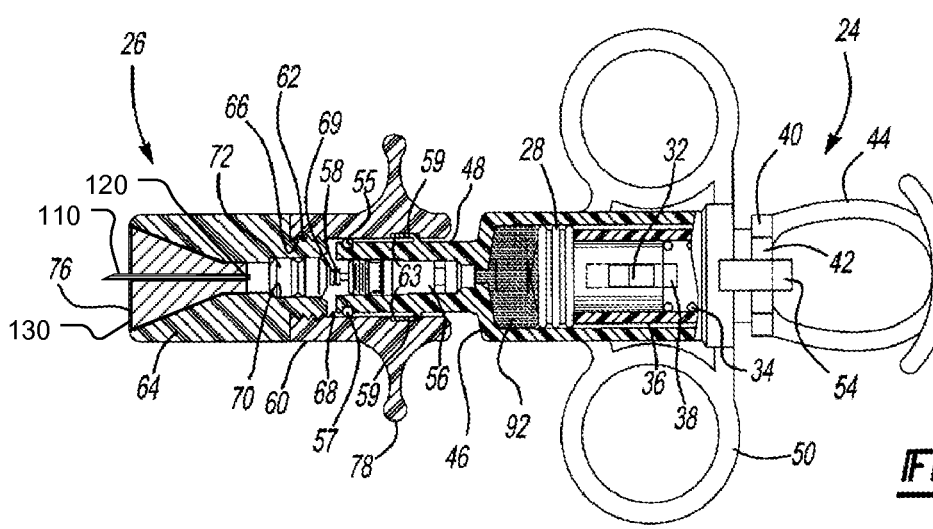
Figure 5:
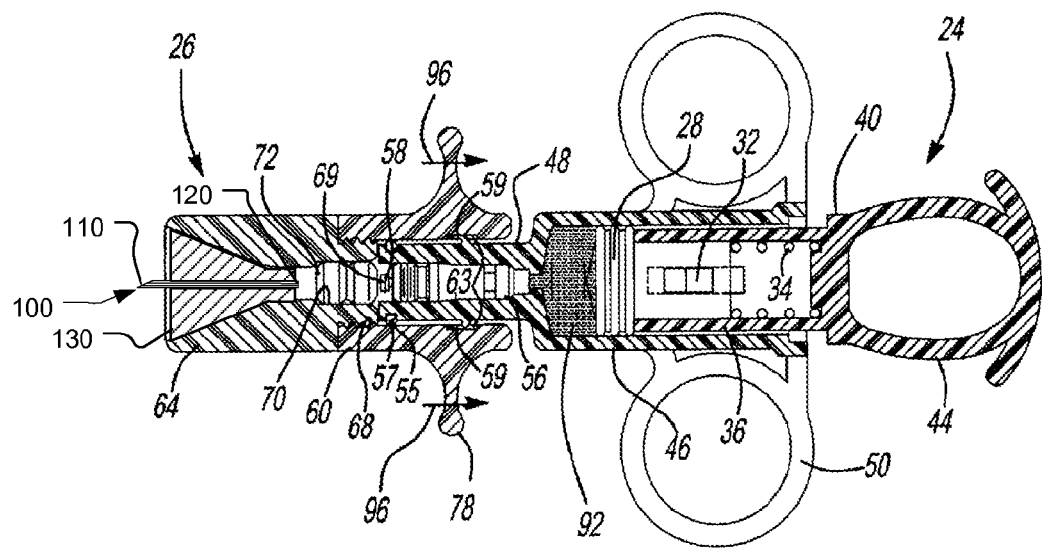
Figure 6:
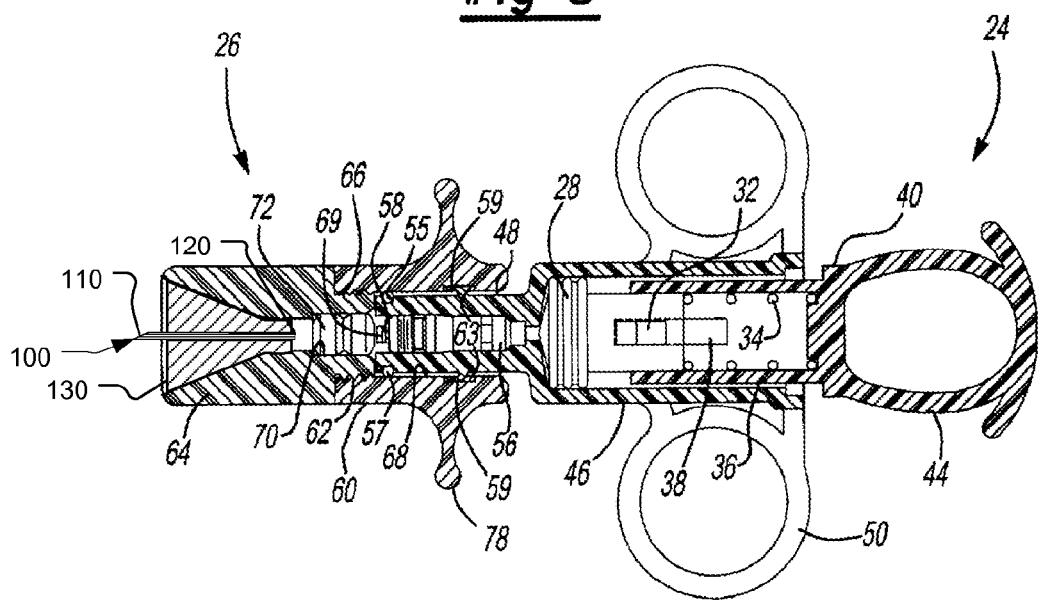

FIGS. 2A and 2B illustrate the assembly of the plunger and stopper assembly 22. The stopper and plunger assembly 22 is assembled by depressing the stopper 28 against the spring 34 until the detent 32 is received in the detent opening or pocket 38. FIG. 9 illustrates in more detail a preferred embodiment of the detent 32 and pocket 38 illustrated in FIGS. 1 to 3. The resilient detent 32 may be integral with the tubular wall 30 of the plunger and preferably includes a ramp portion 31 and a vertical stop portion 33. The detent pocket 38 in the disclosed embodiment is an elongated rectangular opening in the tubular wall 36 of the piston housing having a length sufficient to allow the plunger 30 and stopper 28 to move from a first position as shown in FIGS. 4 and 5 to an extended position as shown in FIG. 6 as further described below. As disclosed below, the detent 32 moves in the detent pocket 38 upon opening of the valve 56 which results in a sudden drop of pressure between the stopper 28 and the outlet of the syringe barrel to sweep fluid in the chamber 92 through the valve 56 and the passage 84 of the cartridge 72. The barrel and valve assembly 24 is assembled in the housing member 60 of the housing and cartridge member 26 by first inserting the Schraeder valve 56 in the open end 49 of the tubular barrel 46, disposing the O-ring 57 in the annular groove 55 and then Inserting the reduced diameter tip portion 48 into the bore 68 of the housing member 60. During insertion of the reduced diameter tip portion 48 in the bore 68 of the housing member 60, the resilient L-shaped tabs 59 are received in the elongated grooves 63 in the bore 68 which slidably locks the housing member 60 on the reduced diameter tip portion 48 and prevents rotational movement of the housing member 60 on the barrel 46 following assembly. As described below, the housing member 60 is telescopically moved on the reduced diameter tip portion 48 by the patient to actuate or open the valve 56 and the O-ring 57 adjacent the open end 49 of the reduced diameter tip portion 48 seals the passage between the valve outlet and the medicament cartridge 72. The housing and cartridge assembly 26 is assembled by first inserting the medicament cartridge 72 in the chamber 70 in the second housing member 64 and then threading the male threaded portion 66 into the female threaded portion 62 as shown in FIG. 3.

Figure 3:
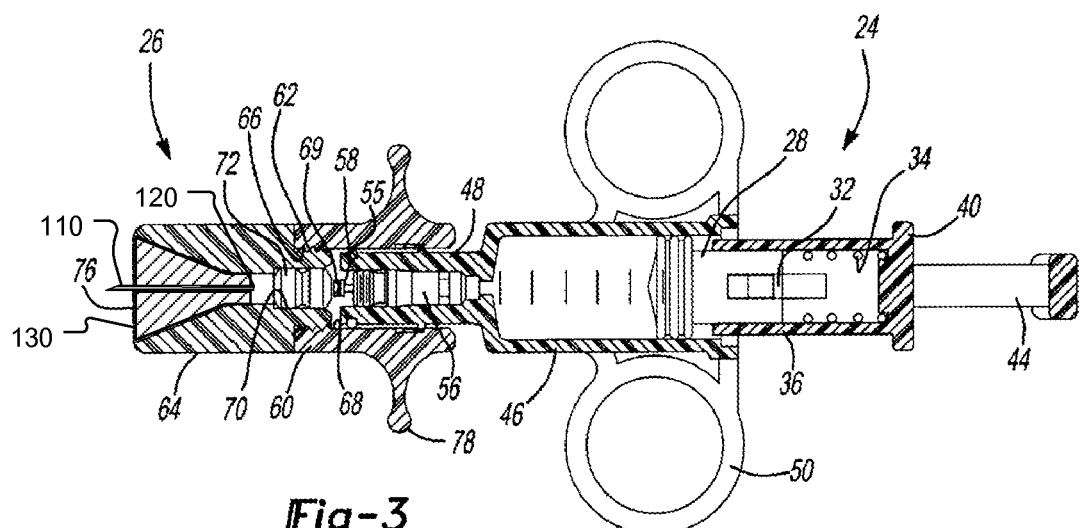

The assembled plunger and stopper assembly 22 is inserted into the open end 53 of the barrel and valve assembly 24 as shown in FIG. 3. As will be understood, the plunger and stopper assembly 22 and the barrel and valve assembly 24 may be assembled in the housing member 60 as described above by the manufacturer of the medicament delivery device 20 of this invention, such that the patient need only assemble the medicament cartridge 72 in the port or passage 68 following each use by unthreading the housing member 64 from the housing member 60 as described above. The medicament delivery device is then ready for use.

Figure 7:
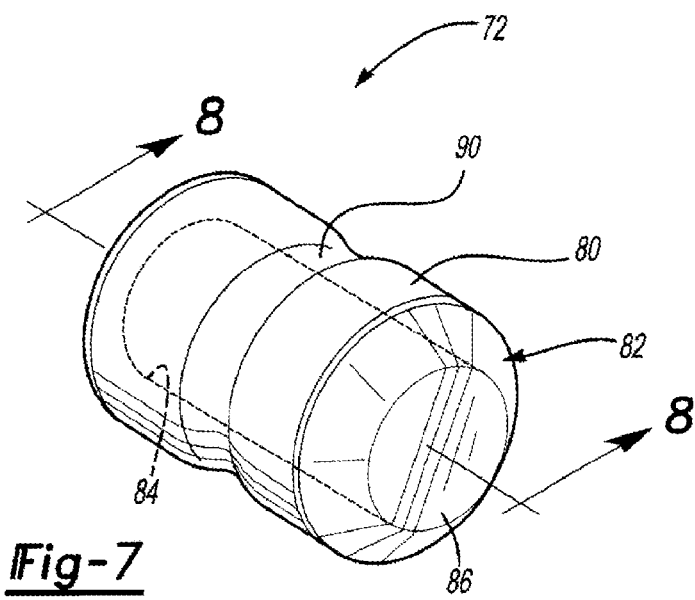
Figure 8:
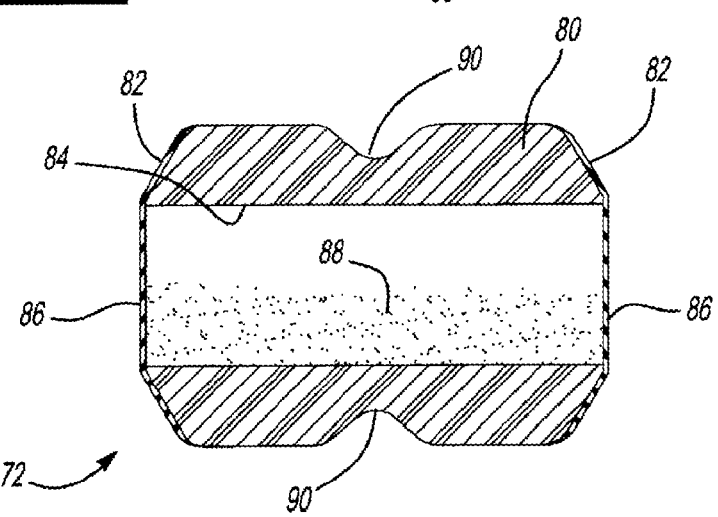
Figure 9:
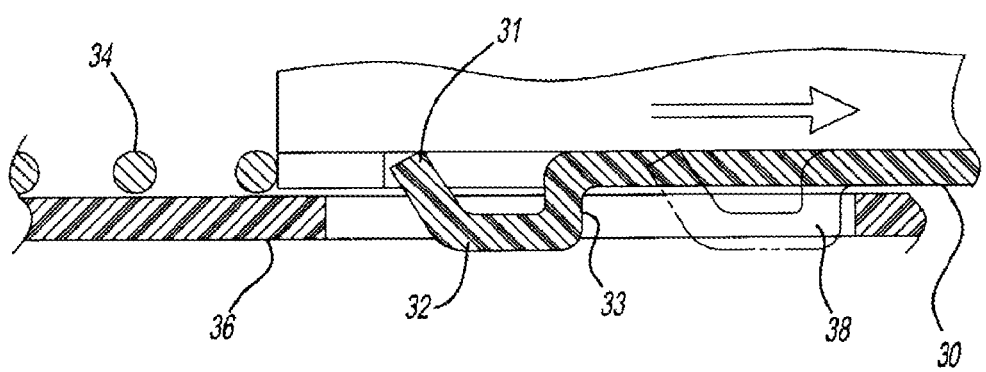

FIGS. 7 and 8 illustrate a preferred embodiment of the medicament cartridge 72, which is disclosed in more detail in the above-referenced co-pending patent application. The medicament cartridge 72 includes a generally cylindrical body 80 which may be formed by injection molding a suitable polymer, such as polyethylene. The body 80 includes opposed end portions 82 which, in the preferred embodiment, are convex, most preferably frustoconical as shown. The cartridge body 80 includes a cylindrical passage 84 through the end portions 82 and a medicament 88 is disposed within the sealed cartridge. In the disclosed embodiment, the body 80 includes a V-shaped groove 90 for ease of handling because the cartridge is relatively small. The opposed ends 82 of the cartridge are preferably convex such that the burstable membranes 86 may be stretched taut over the surface of the end portions 82 prior to bonding of the membranes to the ends 82 of the cartridge body. Because the burst pressure of the membranes 86 is relatively low, less than 10 atmospheres or more preferably less than 5 atmospheres, the membranes 86 are preferably stretched taut to assure a reproducible rupture pressure as discussed further below. As disclosed more fully in the above-referenced co-pending patent application, the cartridge 72 may be formed by first heat bonding one membrane to one end 82 of the cartridge, wherein the membrane is first stretched taut over the frustoconical end 82 of the cartridge and then heat fused to the cartridge by a suitable die (not shown). The medicament 88 is then inserted into the cartridge through the opposed open end of the passage 84. The opposed end of the passage 84 is then sealed by applying a second burstable membrane to the opposed convex end 82 of the cartridge by stretching the membrane over the frustoconical end and heat bonding the opposed membrane to the opposed end, sealing the cartridge. As set forth above, the medicament 88 may be a fine powder medicament, vaccine or drug or a liquid medicament, drug, diagnostic agent, cellular therapy or vaccine or combinations thereof which may be administered by an injection delivery aspect of the invention. In other aspects of the invention, the administration of same compounds is through the user's nose or mouth to the patient's respiratory system. In yet other aspects of the invention, the administration of same compounds is through any orifice. The delivery device delivers a predetermined quantity or dose of medicament with each application.

In one particular embodiment of the cartridge 72, the burstable membranes 86 are formed from a thin sheet of a polyolefin, most preferably polyethylene, a polyethylene blend or copolymer having a thickness of between 0.5 and 1.5 mils and a burst pressure of less than 10 atmospheres, preferably less than 5 atmospheres, and most preferably between 1.5 and 4 atmospheres. As disclosed more fully in the above-referenced co-pending patent application, the burstable membranes may be formed of a preferentially oriented or uniaxially oriented polyolefin film, wherein the burstable membranes on the opposed ends 82 of the cartridge are oriented at approximately at right angles. As described below, the burstable membranes 86 on opposed ends 82 of the cartridge rupture substantially simultaneously when fluid under pressure is received through the passage 68 of the housing and cartridge assembly 26. Where the burstable membranes 86 comprise preferentially or uniaxially oriented burstable films and the films are oriented at approximately right angles, the films rupture in slits generally at or near the center of the passage 84 along the orientation of the film, causing the fluid, preferably air, to turn through the passage 84, entraining the medicament 88 and expressing the entrained medicament through the perpendicular slit formed in the opposed membrane. It has been found by the applicant that generally perpendicular orientation of the preferentially or uniaxially oriented films, wherein the films are oriented at approximately right angles results in an admitted dose of about 97% in a respiratory embodiment. As set forth below, however, other polyolefin films may be used for the burstable membranes 86.

The next step in charging the medicament delivery device 20 is driving the plunger and stopper assembly 22 through the tubular barrel 46 toward the reduced diameter tubular tip portion 48 to create a pressure chamber 92 between the stopper 28 and the inlet to the valve 56 as shown in FIG. 4. This is accomplished by inserting the thumb of the patient into the thumb grip 44, gripping the finger grips 50 and depressing the thumb. The plunger and stopper assembly 22 is then rotated as shown by arrow 94 in FIG. 1, whereby the radial locking tabs 42 are received in the hook-shaped tabs 54, locking the plunger and stopper assembly 22 in the position shown in FIG. 4. Other detenting and locking means may be utilized without departing from the scope of the invention. The medicament delivery device 20 is thereby armed and ready for expressing the medicament 88 in the cartridge 72 as now described.

The patient then turns the medicament delivery device 20 to receive the needle 100 of the housing and cartridge assembly 26 in the patient's body, usually by a penetrating insertion for delivery of the medicament. The patient then grips the finger grip 78 of the housing and thump grip 44 and then compresses the housing and cartridge assembly 26 toward the barrel and valve assembly 24, which causes the bar 69 opposite the valve stem 58 bridging the internal surface of the first housing member 60 to depress the valve stem 58 as shown in FIG. 5, opening the valve 56. During telescopic movement of the housing and cartridge assembly 26 toward the barrel and valve assembly 24 as shown by arrows 96 in FIG. 5, the L-shaped tabs 59 on the reduced diameter tip portion 48 travel or slide in the elongated grooves or slots 63 in the housing member 60, preferably the full length of the groove 63, such that the groove 63 provide a positive stop for movement of the housing member 60 and prevent rotation of the housing and cartridge assembly 26 on the barrel and valve assembly 24 during actuation of the valve. Fluid under pressure is then received in the inlet opening 68, substantially simultaneously rupturing the burstable membranes 86 at the opposed ends of the medicament cartridge 72 and expressing the entrained and/or dissolved medicament through the needle 100 as shown in FIG. 5. The sudden reduction of pressure in the pressure chamber 92 (FIG. 5) resulting from opening of the valve 56 drives the stopper 28 to the end of the chamber 92 as shown in FIG. 6 under the force of the coil spring 34 to sweep remaining fluid in the barrel 46 through the housing and cartridge assembly 26, completing the delivery of medicament to the patient.

The patient then releases the finger grip 78 and replaces the cartridge 72 for reuse by unthreading the housing member 64 from the housing member 60. Alternatively, the housing member 64 may be releasably interconnected to the housing member 60 by other suitable mechanisms including conventional detents and detent pockets, bayonet connections, etc. Except for the cartridge 72, the medicament delivery device 20 of this invention is reusable. Further, it should be noted that the cartridge 72 can be inserted into the chamber 70 of the housing and cartridge assembly 26 in either orientation, thereby avoiding error. The medicament delivery device thereby delivers a controlled dose of a medicament on demand. That is, the patient can charge or pressurize the medicament delivery device prior to use, such that the patient does not have to simultaneously pressurize the pressure delivery device with the needle inserted into the body while injecting the medicament.

Prototype testing of the medicament cartridge 72 illustrated in FIGS. 7 and 8 in a test fixture with perpendicular uniaxially oriented polyethylene films having a thickness of about 1 mil having a burst pressure of about 3 atmospheres resulted in an emitted dose of about 97% of a powder medicament having a particle size of 1 to 5 microns, for respiratory delivery. Burst tests of burstable membranes were conducted by the Applicant using a syringe as shown to deliver gas under pressure to a cartridge in a test fixture simulating the medicament delivery devices of this invention. The cartridge was formed as described herein having a surface area of 0.049 $in^2$ (3 mm diameter) covering the passage. The stopper was moved through the barrel under controlled conditions at 25 in/min and the burst pressure (force divided by area) and emitted dose (i.e. percentage of powder emitted from the passage, HPLC assay) was measured. The preferred particle size for intranasal delivery is 50 to 100 microns. 1 to 5 microns is preferred for pulmonary delivery of powder medicament, such as insulin. The applicant also tested other burstable films or membranes with the following results. A cast 50/50 copolymer of ethylene and methylacrylate having a thickness of 0.5 mil and burst pressure of about 2 atmospheres resulted in an emitted dose of about 95% in the respiratory embodiment.

As used herein, "polyolefin" includes polymers derived from simple olefins including polyethylene, polypropylene, polybutenes, etc., copolymers and blends. As used herein, "polyethylene," includes polyethylene blends and copolymers with and without additives. Uniaxially oriented polyethylene films having a thickness of about 0.5 mil having a burst pressure of about 3 atmospheres, wherein the films were oriented approximately parallel, resulted in a 93% emitted dose rate in a respiratory embodiment. The applicant also tested a polyethylene film having a thickness of about 0.9 mil wherein the polyethylene film had a checker board embossment having a burst pressure of about 3 atmospheres, wherein the emitted dose rate was about 91% in a respiratory embodiment. Thus, in one aspect of the invention the embodiments of the cartridge for a medicament delivery device of this invention include burstable membranes formed of polyethylene film having a thickness of between about 0.3 mil to about 1.5 mil, wherein the preferred range is between 0.5 and one mil and a burst pressure of between 1.2 and 10 atmospheres or more preferably less than 5 atmospheres and most preferably between 1.5 and 4 atmospheres. It is believed, however, that films formed of other polymers may be used including, for example, polypropylene, acetate and polycarbonate; however, it is also believed that such other films should be scored or embossed to reduce the burst pressure.

As will be understood, the medicament delivery device and cartridge of this invention may be utilized to deliver various substances including medicaments, drugs, diagnostic agents, cellular therapies and vaccines or combinations thereof to the system via the parenteral, nasal, pulmonary or buccal routes used in the prevention, diagnosis, alleviation, treatment or cure of diseases. These substances may include, for example, (i) drugs such as Anti-Angiogenesis agents, Antisense, anti-ulcer, butorphanol, Calcitonin and analogs, COX-II inhibitors, desmopressin and analogs, dihydroergotamine, Dopamine agonists and antagonists, Enkephalins and other opioid peptides, Growth hormone and analogs (including growth hormone releasing hormone), Growth hormone antagonists, IgE suppressors, Insulin, insulinotropin and analogs, Ketamine, Kytril, Leutenizing hormone releasing hormone and analogs, lidocaine, metoclopramide, Midazolam, Narcotic analgesics, neuraminidase inhibitors, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, vasopressin; (ii) vaccines with or without carriers/adjuvants such as prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, arthritis, cholera, cocaine addiction, HIB, meningococcus, measles, mumps, rubella, varicella, yellow fever, Respiratory syncytial virus, pneumococcus, streptococcus, typhoid, influenza, hepatitis, including hepatitis A, B, C and E, polio, HIV, parainfluenza, rotavirus, CMV, chlamydia, non-typeable haemophilus, moraxella catarrhalis, human papilloma virus, tuberculosis including BCG, gonorrhea, asthma, atheroschlerosis, malaria, otitis media, *E-coli*, Alzheimers, H. Pylori, salmonella, diabetes, cancer and herpes simplex; and (iii) other substances in all of the major therapeutics such as Agents for the common cold, Anti-addiction, anti-infectives, analgesics, anesthetics, anorexics, antiarthritics, anti-allergy agents, antiasthmatic agents, anticonvulsants, anti-depressants, antidiabetic agents, anti-depressants, anti-diuretics, anti-emetics, antihistamines, anti-inflammatory agents, antimigraine preparations, antimotion sickness preparations, antinauseants, antineoplastics, anti-obesity, antiosteoporeteic, antiparkinsonism drugs, antipruritics, antipsychotics, antipyretics, antitussiers, anticholinergics, benzodiazepine antagonists, bone stimulating agents, bronchial dilapors, central nervous system stimulants, corticosteroids, hormones, hypnotics, immunosuppressives, mucolytics, prostaglandins, proteins, peptides, polypeptides and other macromolecules, psychostimulants, rhinitis treatment, sedatives, sexual hypofunction, tranquilizers and vitamins including B12.

As will be understood by those skilled in this art, various modifications may be made to the disclosed embodiment of the medicament delivery device 20 of this invention within the purview of the appended claims. For example, the passage 84 through the cartridge body 80 shown in FIG. 8 may be bell-shaped or other shapes, although cylindrical is desirable, particularly with the relatively low fluid pressure delivered by the pressure delivery device. Further, a conventional syringe assembly may be utilized having a conventional plunger and stopper; however, it is desirable to lock the stopper in the extended position such that the patient does not have to hold the stopper while opening the valve. Further, a conventional Schraeder valve operable at low pressures has been utilized in the medicament delivery device of this invention, although various types of valves and valving systems may be utilized. The Schraeder valve 56 may also be reversed, such that the valve stem 58 extends into the syringe barrel 46, wherein the valve is opened by engagement with the stopper 28. In this embodiment (not shown), the valve may be opened either by depressing the stopper 28 against the valve stem 58 to open the valve or more preferably, the medicament housing member 60 may be movable relative to the syringe barrel (as shown) to drive the valve stem 58 against the stopper 28 and open the valve, such that the valve may be opened on demand by the patient during use. As used herein, valve "inlet" and "outlet" will depend upon the orientation of the valve and is used merely to define the valve openings which receive and exhaust the fluid pressure. It is desirable however to use a valving system which may be easily opened on demand by the patient during use. Other pressure delivery devices may also be utilized, including collapsible bulbs as disclosed in the above-referenced co-pending application, wherein a separate pressure chamber is provided between the bulb and the valve with a one way check valve between the bulb and the pressure chamber. Further, other locking mechanisms may be utilized to releasably interconnect the plunger and stopper assembly 22 in the barrel and valve assembly 24 following pressurization or charging of the chamber 92 including, for example, bayonet-type connections, a separate locking member and interlocking detents and detent pockets.

Further, the cartridge may include only one polymeric burstable membrane, preferably at the outlet, wherein the membrane at the inlet is a pierceable film or a film which is removed prior to use. Other types of membranes may also be used to seal the medicament cartridge or medicament chamber of the housing, including "nonburstable" membranes, for example, which are preslit to open at a pressure of less than 10 atmospheres, preferably less than 5 atmospheres, and most preferably oriented at right angles. As used herein, the term "open" the membranes is intended to be generic to either busting or rupturing burstable membranes as disclosed herein or dilating preslit membranes. Further, although a replaceable medicament cartridge is desirable to permit reuse of the housing or dosing member, the cartridge may be eliminated by sealing the inlet and outlet of the housing chamber with membranes. Finally, although the medicament delivery device of this invention was developed for delivery of a powder medicament, the cartridge of this invention is suitable for delivery of a liquid or even a gaseous medicament and the barrel 46 may also contain a liquid medicament or diluent, wherein the cartridge includes a powder medicament. Alternatively, the barrel 46 may also contain a powder medicament or compound, wherein the cartridge includes a liquid medicament. Furthermore, the barrel 46 may also contain a fluid medicament or diluent, wherein the cartridge includes a liquid medicament. Having described a preferred embodiment of the medicament delivery device, the invention is now claimed, as follows.

The invention claimed is:

1. An apparatus for mixing a fluid and medicament within a medicament delivery device, comprising:
   a pressure member comprising a barrel, a movable stopper located therein and a telescopic plunger engaged to said movable stopper, said telescopic plunger having a biasing spring therein and said pressure member having a pressure member outlet, said pressure member having a first and a second position;
   a valve having an outlet and an inlet in fluid communication with said pressure member outlet;
   a stop member comprising releasable cooperating detents on said barrel and said telescopic plunger wherein said stop member retains said pressure member in said second position wherein said releaseable cooperating detents are adapted to withstand the resultant force generated by retention of said pressure member in said second position;
   a medicament dosing member having a chamber therein including a chamber inlet in fluid communication with said valve outlet and a chamber outlet, a medicament in said chamber and membranes sealing said chamber inlet and outlet; and
   a needle having a distal end and a proximal end wherein said proximal end is in fluid communication with said chamber outlet and said distal end is adapted for parenteral delivery;
   whereby transition of said pressure member from said first position to said second position generates fluid under pressure at said pressure member outlet and opening of said valve releases fluid under pressure into said chamber inlet, breaching said membranes and expressing said medicament in said chamber through said chamber outlet, and through said needle.

2. The apparatus as defined in claim 1, further comprising a penetration member adapted for breaching said membrane covering the chamber inlet wherein breaching of said membrane covering the chamber inlet is by application of said penetration member, and said penetration member penetrates said membrane covering the chamber inlet.

3. The apparatus as defined in claim 1, wherein said releasable cooperating detents are engaged by relative rotation between said telescopic plunger and said barrel in order to retain pressure member in said second position.

4. The apparatus as defined in claim 3, wherein said valve is manually releasable.

5. The apparatus as defined in claim 1, wherein said distal end of said needle is sharpened.

6. The apparatus as defined in claim 1, wherein said pressure member is a syringe.

7. The apparatus as defined in claim 1, wherein said medicament is a liquid.

8. The apparatus as defined in claim 1, wherein said medicament is a powder.

9. The apparatus as defined in claim 1, wherein said membranes are burstable and formed of a polyolefin having a burst pressure of less than 10 atmospheres.

10. The apparatus as defined in claim 9, further comprising a penetration member wherein breaching of said membranes is by application of said penetration member, wherein said penetration member penetrates said membranes.

11. A medicament delivery device, comprising:
    a medicament dosing member including a chamber having a chamber inlet and a chamber outlet generally co-axially aligned with said chamber inlet;
    a medicament cartridge located within said chamber having opposed ends, a passage through said medicament cartridge through said opposed ends generally co-axially aligned with said chamber inlet and chamber outlet of said medicament dosing member, a medicament in said passage and breachable membranes sealing said passage at said opposed ends of said cartridge;
    a fluid delivery device including a tubular barrel having a barrel outlet in fluid communication with said chamber inlet, a telescopic plunger located within said tubular barrel said telescopic plunger having a biasing spring therein, and manually movable from a first position within said tubular barrel to a second position toward said barrel outlet, thereby compressing fluid within said tubular barrel at said barrel outlet and said tubular barrel and said telescopic plunger including cooperative stop members retaining said telescopic plunger in said tubular barrel when said telescopic plunger is moved in said tubular barrel to generate a fluid pressure within said tubular barrel at said tubular barrel outlet;
    a valve located between said barrel outlet and said chamber inlet having a valve inlet in fluid communication with said barrel outlet and a valve outlet in fluid communication with said chamber inlet; and
    a stop member fixing said telescopic plunger in said tubular barrel at said second position said stop member comprising releasable cooperating detents on said tubular barrel and said telescopic plunger engageable by relative rotation between said tubular barrel and said telescopic plunger wherein said stop member retains said telescopic plunger in said second position; and
    a needle having a distal end and proximal end wherein said proximal end is in fluid communication said chamber outlet and said distal end is adapted for parental delivery;
    whereby movement of said telescopic plunger from said first position to said second position compresses fluid in said tubular barrel at said barrel outlet and opening of said valve delivers fluid under pressure to said chamber inlet, and expressing said medicament through said chamber outlet and through said needle.

12. The medicament delivery device as defined in claim 11, wherein said medicament in said passage is a powdered medicament.

13. The medicament delivery device as defined in claim 11, wherein said medicament in said passage is a liquid medicament.

14. The medicament delivery device as defined in claim 11 further comprising a penetration member adapted for breaching said membrane covering the chamber inlet, wherein said breaching of said membrane covering the chamber inlet is by application of said penetration member, wherein said penetration member breaches said membrane covering the chamber inlet.

15. The medicament delivery device as defined in claim 14 wherein said penetration member is a portion of said valve.

16. The medicament delivery device as defined in claim 11, wherein said medicament dosing member is movable toward said fluid delivery device to open said valve.

17. The medicament delivery device as defined in claim 16 further comprising a penetration member which is a portion of said valve adapted for breaching said membrane covering the chamber inlet, wherein said breaching of said membrane covering the chamber inlet is by application of said penetration member, and said penetration member breaches said membrane covering the chamber inlet.

* * * * *